United States Patent
Grason

(10) Patent No.: US 8,186,478 B1
(45) Date of Patent: May 29, 2012

(54) MULTI-FUNCTIONAL DUAL FILTERED HEARING PROTECTOR

(76) Inventor: Rufus Leroy Grason, Rindge, NH (US)

(*) Notice: Subject to any disclaimer, the term of this patent is extended or adjusted under 35 U.S.C. 154(b) by 0 days.

(21) Appl. No.: 12/930,766

(22) Filed: Jan. 18, 2011

(51) Int. Cl.
*G10K 11/00* (2006.01)
(52) U.S. Cl. ......... 181/175; 181/129; 181/135; 600/559
(58) Field of Classification Search .................. 181/175, 181/135, 129; 600/559
See application file for complete search history.

(56) References Cited

U.S. PATENT DOCUMENTS

| | | | | |
|---|---|---|---|---|
| 5,936,208 A * | 8/1999 | Hamery | ......... | 181/135 |
| 6,070,693 A * | 6/2000 | Hamery | ......... | 181/135 |
| 6,401,859 B1 * | 6/2002 | Widmer et al. | ......... | 181/135 |
| 7,740,104 B1 * | 6/2010 | Parkins et al. | ......... | 181/135 |
| 2002/0179365 A1 * | 12/2002 | Meussen et al. | ......... | 181/135 |
| 2006/0042865 A1 * | 3/2006 | Berg et al. | ......... | 181/135 |
| 2006/0042867 A1 * | 3/2006 | Haussmann et al. | ......... | 181/135 |
| 2007/0125590 A1 * | 6/2007 | Oberdanner | ......... | 181/135 |
| 2010/0294285 A1 * | 11/2010 | Turdjian | ......... | 128/867 |

* cited by examiner

*Primary Examiner* — Forrest M Phillips

(57) ABSTRACT

The present embodiment represents a dynamic Multi-Functional Dual Filtered Hearing Protector that will allow the wearer to hear intelligible speech or warning sounds, while the wearer is present in an environment surrounded by loud noise or impact sounds. The automatic attenuation provided by this hearing protector will increase, as the sound pressure levels increase, thus requiring no human intervention. This hearing protector is especially useful in situations where sounds may be produced from unexpected spikes in sound intensity, while still enabling the wearer to hear warning buzzers, or approaching vehicles without compromising safety. By not requiring human adjustment the wearer will be protected from such sounds. In addition to being able to be connected to acoustic transducers, the invention also relates to a custom hearing protector incorporating features of the embodiment, and a method for manufacturing such a custom hearing protector.

9 Claims, 17 Drawing Sheets

Fig. 1 - Multifunctional Dual Filtered Hearing Protector
Rufus Leroy Grason

Fig. 2 - Multifunctional Dual Filtered Hearing Protector
Rufus Leroy Grason

Fig. 3 - Multifunctional Dual Filtered Hearing Protector
Rufus Leroy Grason

Fig. 5 - Multifunctional Dual Filtered Hearing Protector
Rufus Leroy Grason

Rufus Leroy Grason
Multifunctional Dual Filtered Hearing Protector

Fig. 7 - Multifunctional Dual Filtered Hearing Protector
Rufus Leroy Grason
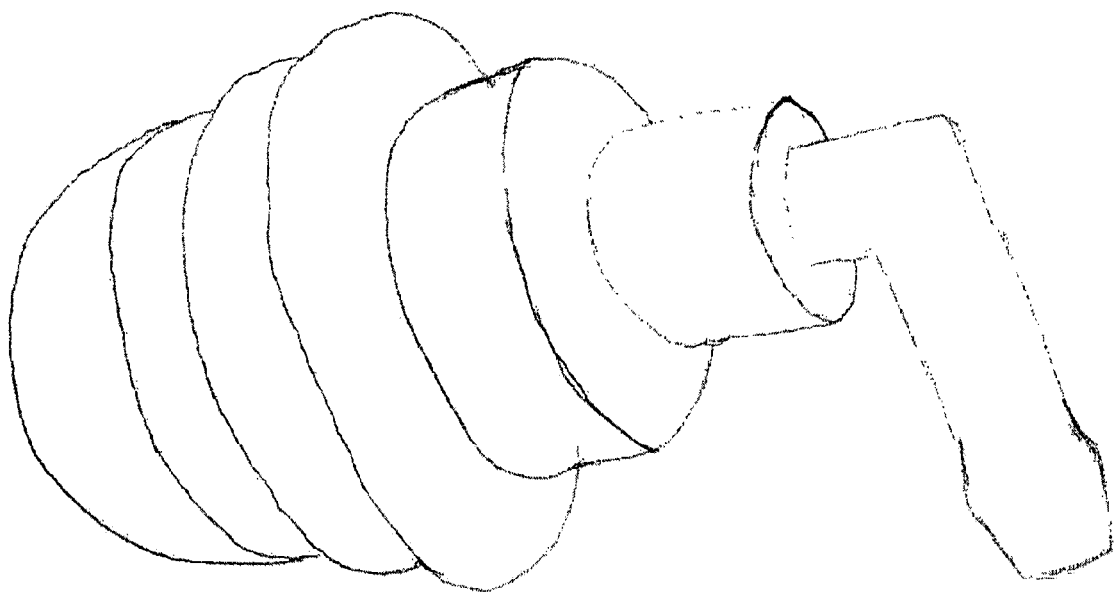

Fig. 8 - Multifunctional Dual Filtered Hearing Protector
Rufus Leroy Grason
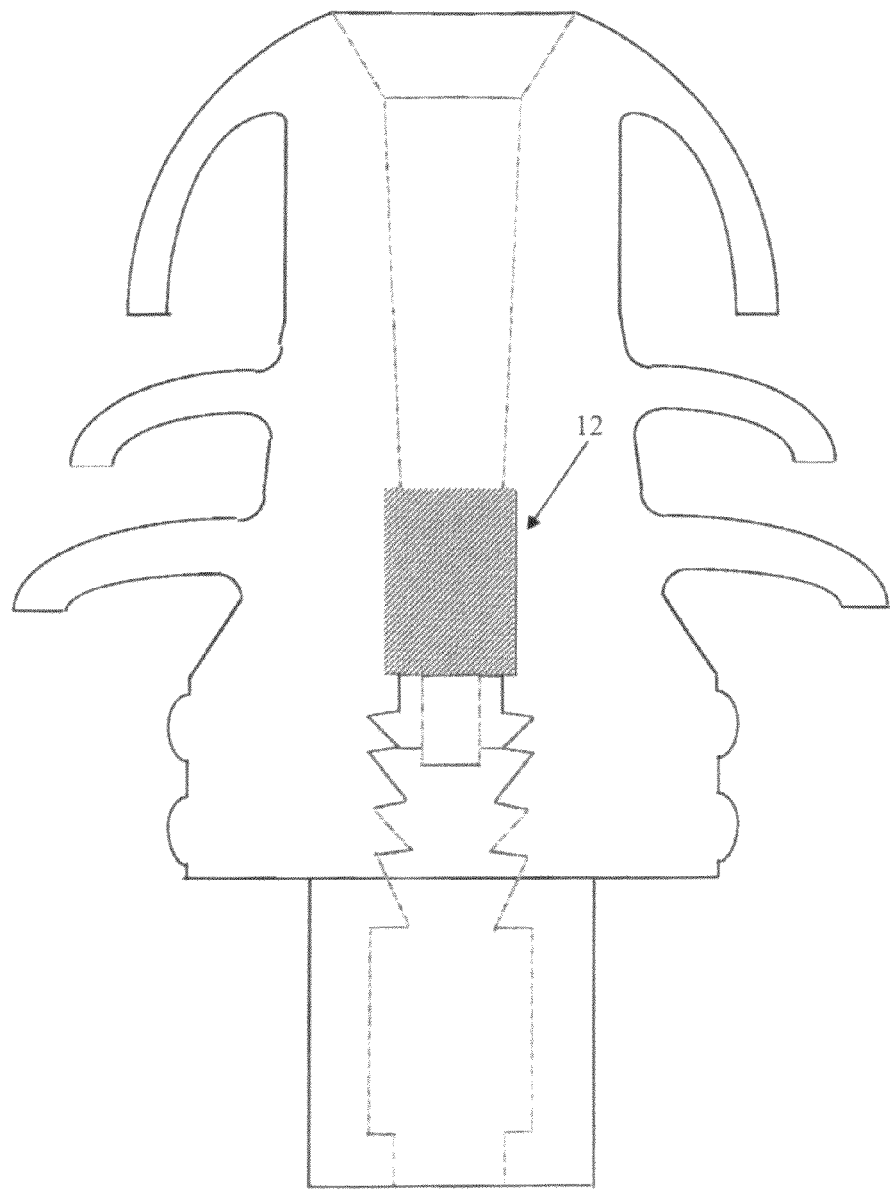
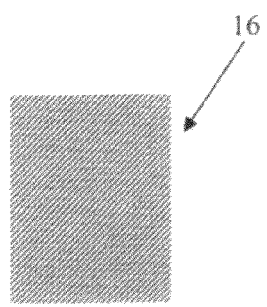

Figure 9
Rufus Leroy Grason
Multifunctional Dual Filtered Hearing Protector
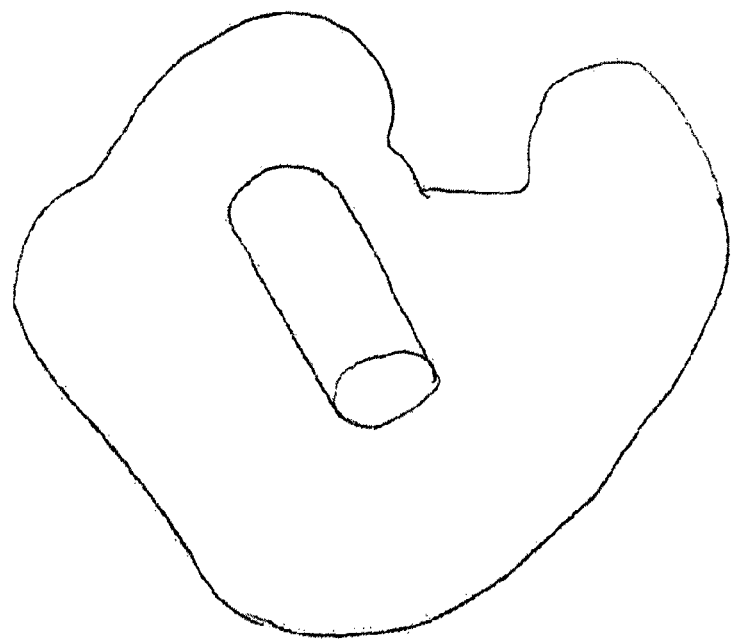
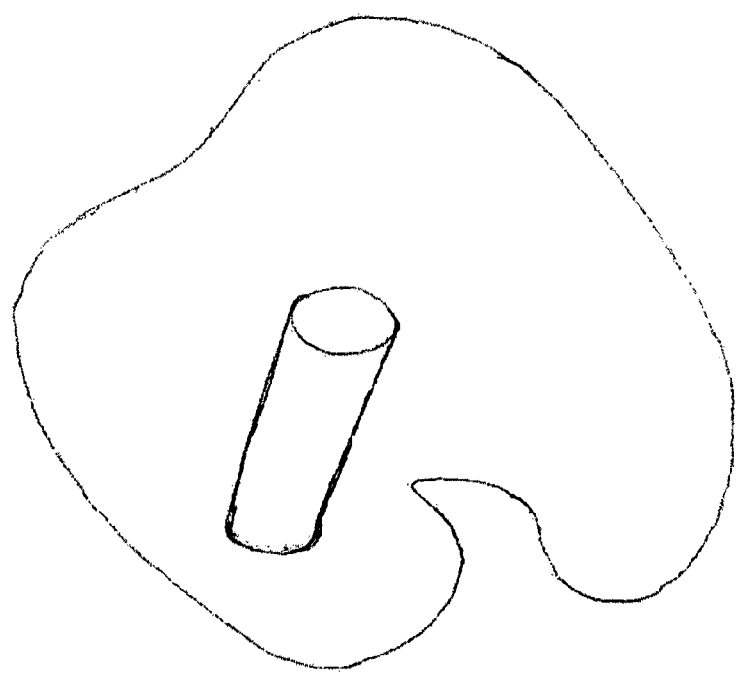

Rufus Leroy Grason, Multifunctional Dual Filtered Hearing Protector
Impulse noise test.
Equipment: ISL head, shocktube, 01dB sound acquisition and analysis.
Date: May 11, 2009

Figure 11 Multifunctional Dual Filtered Hearing Protector
Rufus Leroy Grason
Chamber pressure 1/3 octave
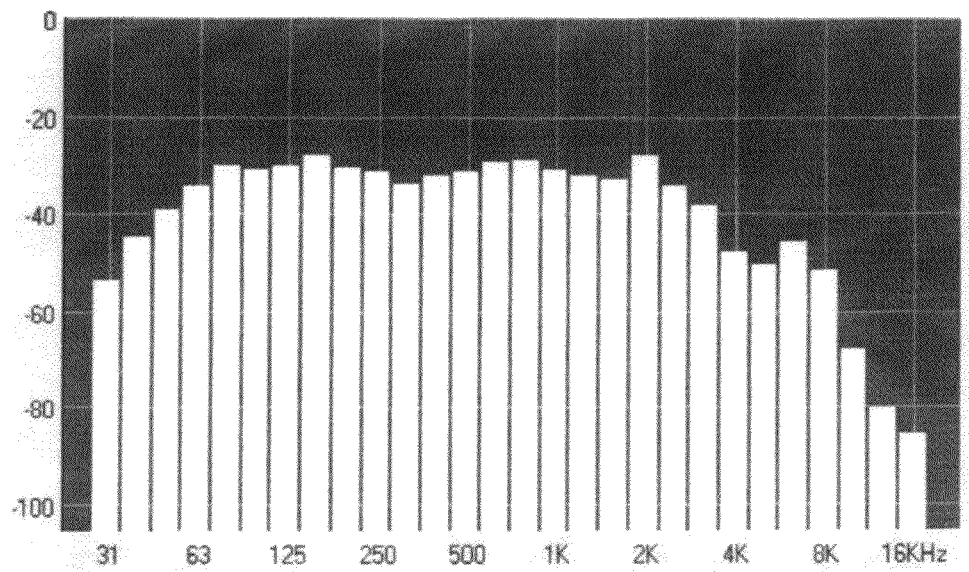
4 port earplug body muffler only no filters
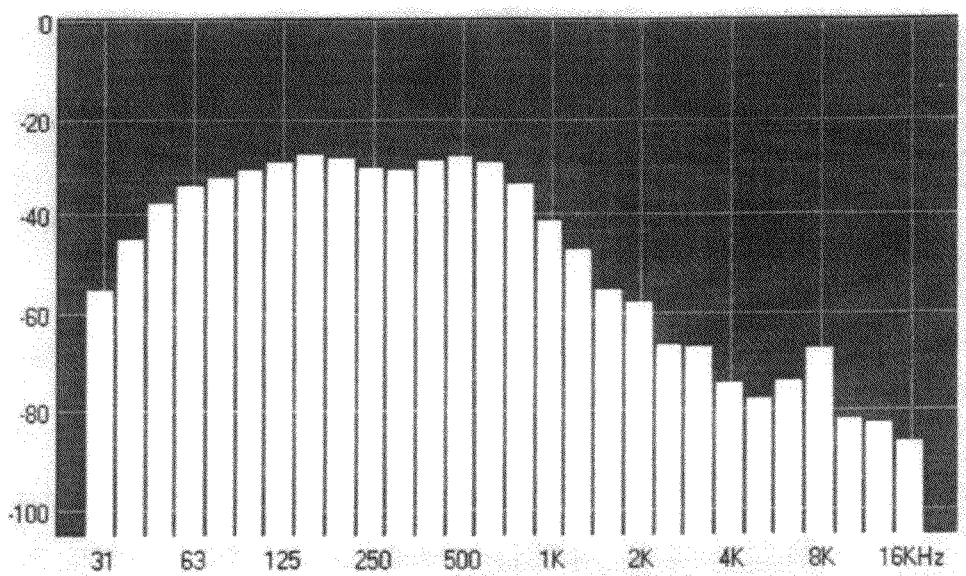

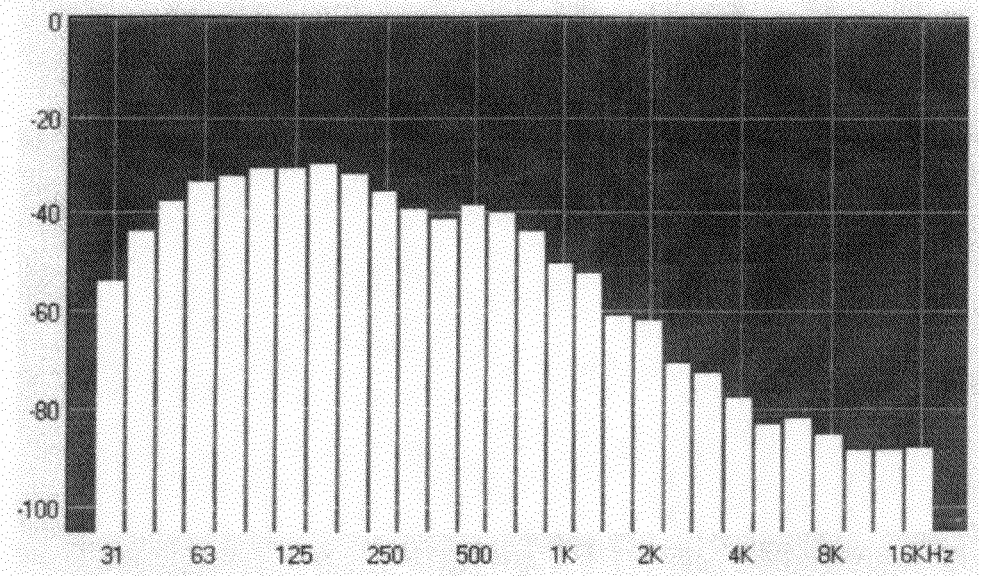
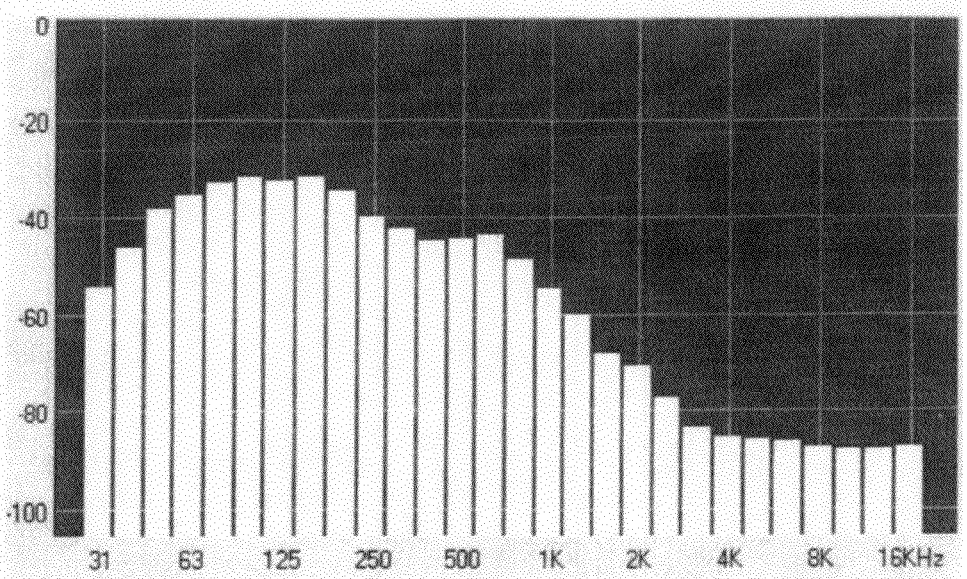
Figure 12 Multifunctional Dual Filtered Hearing Protector
Rufus Leroy Grason Figure 13 Multifunctional Dual Filtered Hearing Protector
Rufus Leroy Grason
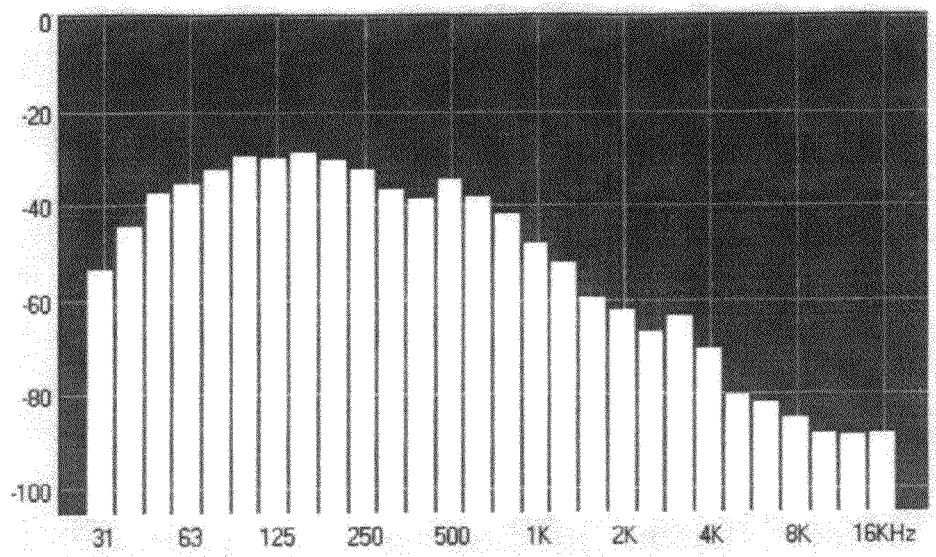
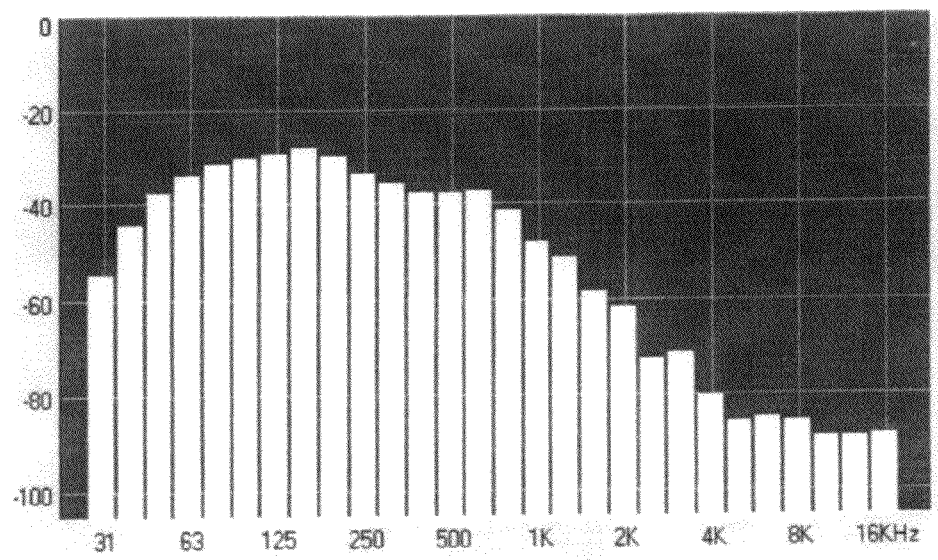

Figure 14 Multifunctional Dual Filtered Hearing Protector
Rufus Leroy Grason
White noise 70 dB input
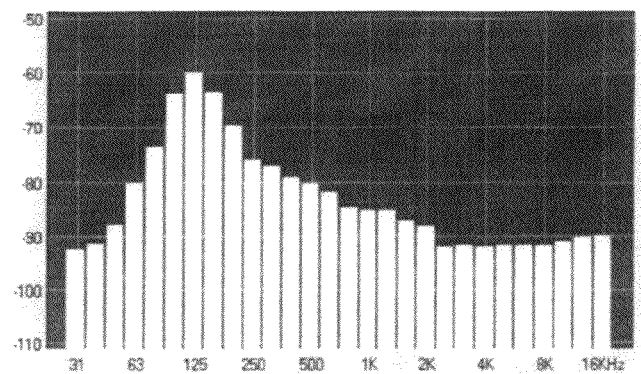
White noise 90 dB input
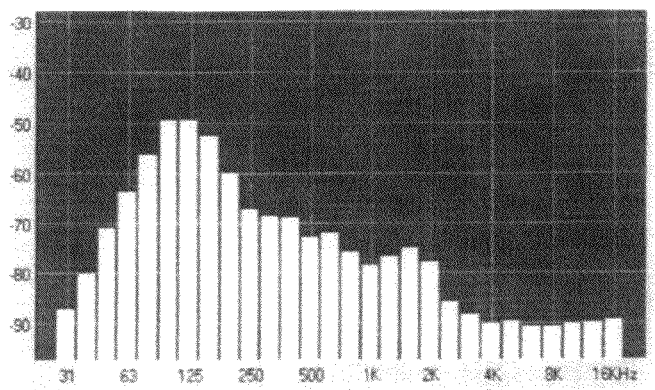
White noise 110 dB input
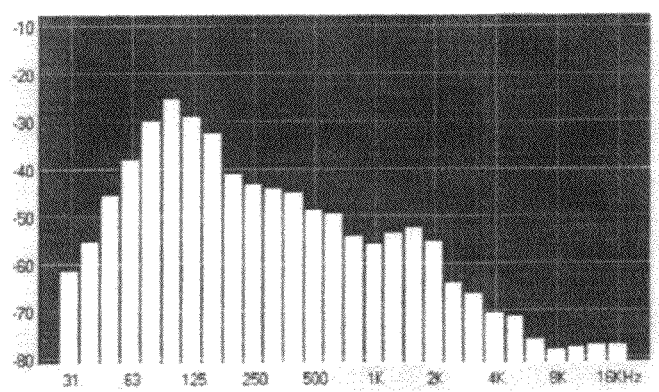

Rufus Leroy Grason
Multifunctional Dual Filtered Hearing Protector

| Frequency Hz | 125 | 250 | 500 | 1000 | 2000 | 3150 | 4000 | 6300 | 8000 |
|---|---|---|---|---|---|---|---|---|---|
| Mean Attenuation | | | | | | | | | |
| A 110 dB | 12 | 16 | 18 | 26 | 35 | 33 | 32 | 41 | 49 |
| B 90 dB | 12 | 17 | 20 | 27 | 39 | 36 | 34 | 30 | 26 |
| C 70 dB | 11 | 16 | 19 | 26 | 35 | 27 | 22 | 14 | 8 |
| D 60 dB | 3 | 6 | 12 | 18 | 27 | 18 | 15 | 8 | 5 |
| E 50 dB | 2 | 5 | 10 | 13 | 20 | 12 | 7 | 3 | 1 |

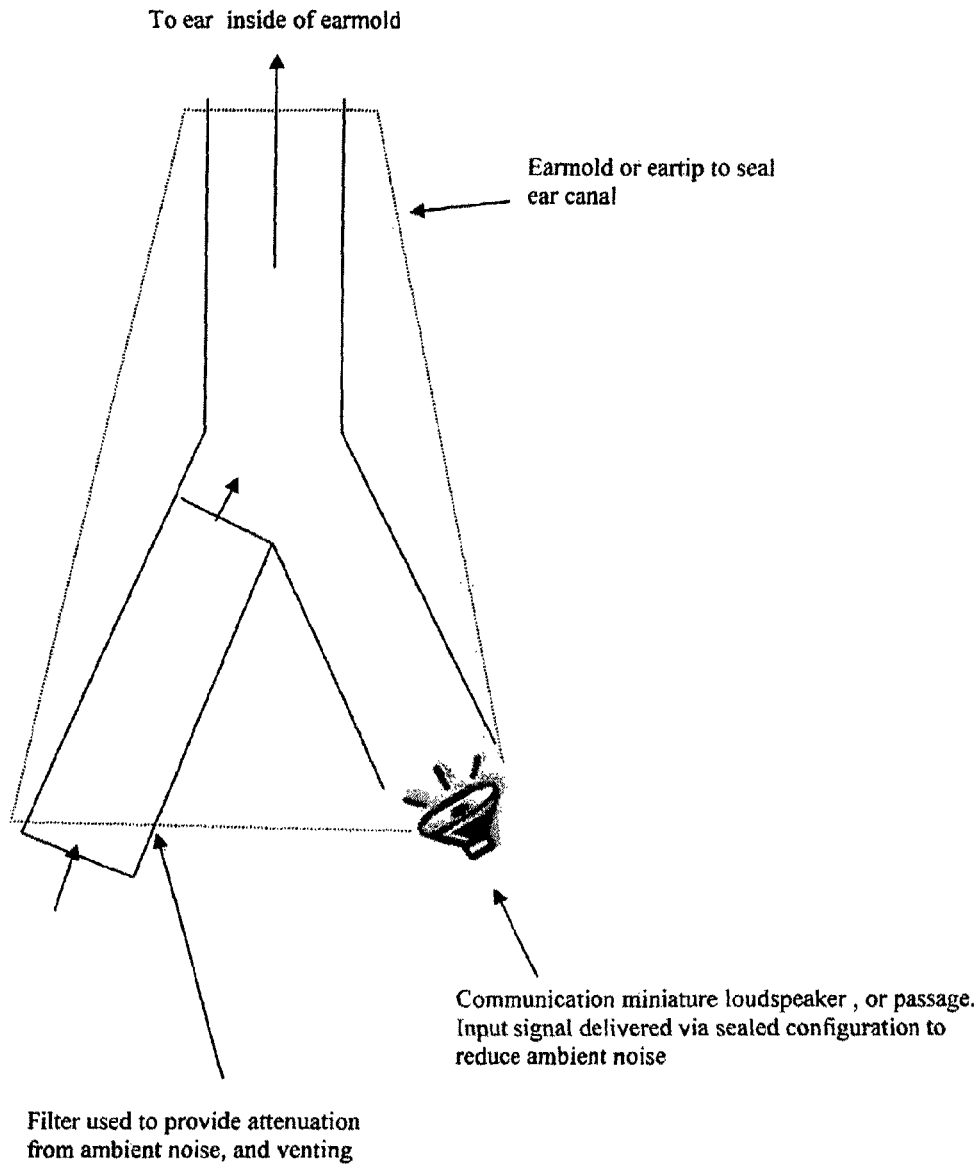
Figure 16 Multifunctional Dual Filtered Hearing Protector
Rufus Leroy Grason
Filter previously described, used in an alternate configuration for a communication headset to reduce the effect of ambient noise on communications and provide protection from external excessive noise

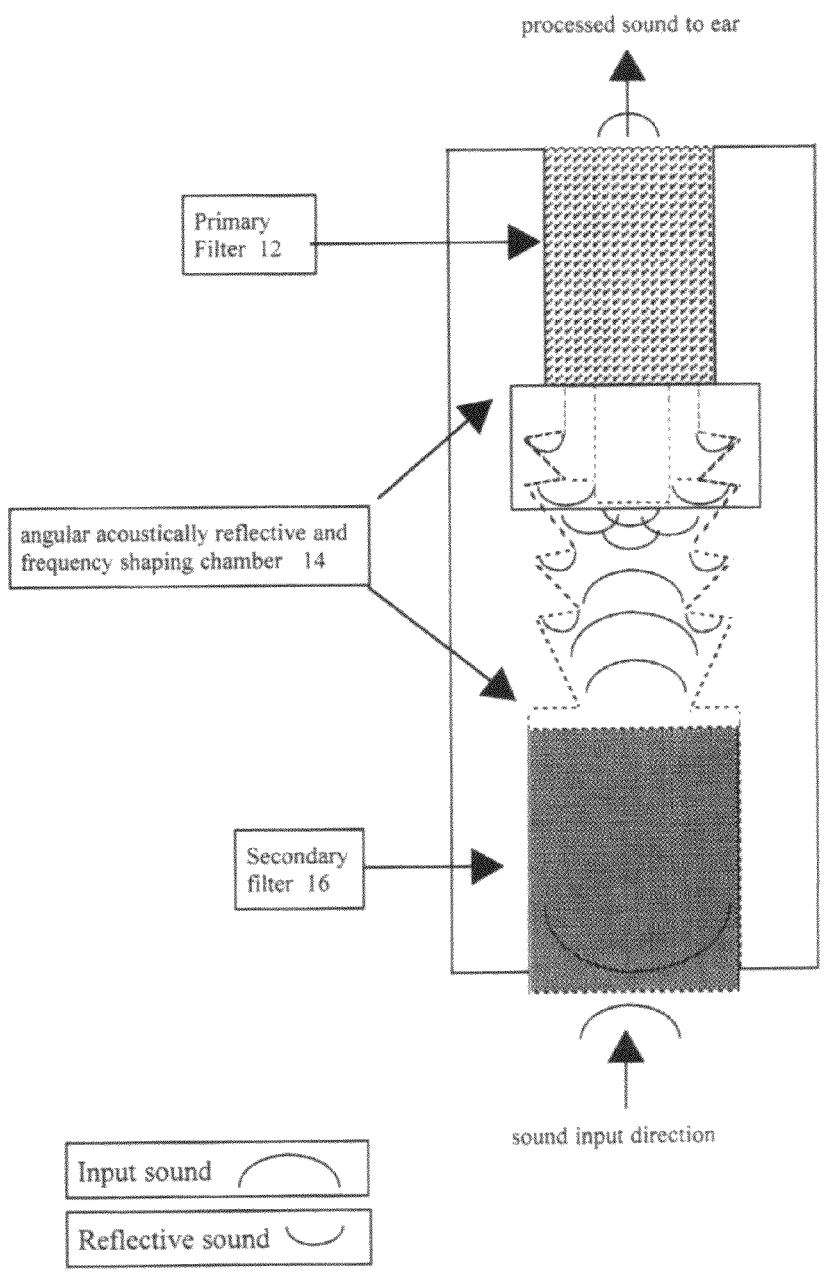

MULTI-FUNCTIONAL DUAL FILTERED HEARING PROTECTOR

This application claims the benefit of provisional patent application Ser. No. 61/335,884 filed Jan. 13, 2010 by the present inventor.

FIELD OF INVENTION

This invention relates to a dynamic earplug that allows the user to hear critical sound including speech while affording protection from loud noises and impact sounds without the need of any user intervention.

BACKGROUND

Prior Art

The following is a tabulation of some prior art that presently appears relevant:
U.S. Pat. Nos.
5,113,967—Audibility Earplug
6,148,821—Selective Nonlinear Attenuating Ear Plug
7,512,243—Hearing Protection Earplug with a Movable Attenuation Button, method for manufacturing the same and use of the same.

General Background

Earplugs are devices meant to be inserted into the ear canal to protect the wearer's ear from loud noises and impact sounds. Their efficacy range from no-sound, muffled sound, distorted sound and reduced sound. To achieve this end, earplugs have been fashioned from various designs with a variety of modern materials and designs for particular environmental conditions, i.e., sleeping, attending rock concerts, shooting, and motorcycling, etc. Additionally, in consideration of prior art, earplugs may be manual (inserted and physically removed by operator intervention) and electronic, noise reduction achieved by the use of sophisticated electronic circuitry.

To indicate the noise reduction capabilities of any earplug, a system of noise reduction ratings (NRR) have been developed. This tells the user, the noise reduction in decibels that can be expected from any such earplug. Decibels work on a logarithmic scale, which means that a reduction of 10 db is roughly equal to reducing the loudness by half. A reduction of 20 db roughly equals a perceived reduction in loudness of 75%.

The three main designs of earplugs today, are the foam, the mold-able wax or silicon style, and the flanged ear or musician earplugs each of which has their own advantages and disadvantages and each of which are better adapted to certain activities then others. The form type as its name implies is made mainly from memory foam, which is compressed and placed into the ear canal where it is allowed to expand and block the ear canal. The silicon earplugs is a device made of silicon or some similar non-toxic substance which is rolled into a ball and carefully molded to fit over the external portion of the ear canal, providing a snug custom fit for the wearer. The flanged earplugs, including most types of musician or hi-fi earplugs, remain the favorite of music lovers, since they attenuate sound evenly across the audio band and thus minimize the effect on the user's perception of bass and treble levels. This is generally achieved by incorporating a tiny diaphragm to reduce low-frequency response, together with absorbent or decking material for high frequency response.

The earplugs herein identified usually given an attenuation of only about 20 db and are not intended for protection from very high noise levels beyond 105 db. Similarly for other activities, hobby motorcyclist and skiers, the ear protection used must be chosen for the use of the decibel reduction to compensate for ongoing noise of the wind against the head or helmet.

Although an earplug's noise reduction rating (NRR) is important, it is meaningless if the ear plug is uncomfortable or can easily be dislodged. Earplug performance and design, from the past to the present, are not the sort of product that one can evaluate simply by judging a sound level rating and moving on to the next brand or type. Choosing the right ear plug is as much a matter of comfort, fit, and ease of insertion as actual noise reduction. Noise is one of the most common causes of hearing loss, and one of the most common occupational illnesses in the United States. A single shot from a shotgun, experienced at close range, may permanently damage hearing in an instant. Repeated exposure to loud machinery may, over an extended period of time, present serious risk to human hearing. Unfortunately, the effects of noise is often underestimated, because the damage takes place so gradually, loud noise has become so common in our culture, and although traumatizing to the parts of the body responsible for hearing, there are no externally visible physical changes like bleeding. As a result, people have traditionally not appreciated the serious impact of noise related hearing loss, until they are frustrated by a permanent communication problem.

When an individual is exposed at work or at home to harmful sounds, those are of the impact type or noise that is too loud over a long period of time, the sensitive structure of the ear can be damaged, causing noise induced hearing loss (NIHL). NIHL is characterized by the gradual progress of loss of high-frequency hearing sensitivity over time as a result of such exposure to excessive noise levels. There is a typical progression of noise induced hearing loss that is usually seen at or near 4000 hertz. In later stages, the hearing loss may spread to frequencies that are more critical to understanding human speech, the range of 500 to 3000 Hz. NIHL usually occurs in both ears. However, the hearing loss may not necessarily occur equally between the left and right ear when the exposure conditions favor one side of the head, as can happen in a acoustic trauma, a loud blast, or explosion, etc. Loud explosions that peak for a few milliseconds at levels greater than 130 db, may cause said hearing loss. More often however, this loss is caused by repeated exposure to noise levels above 85 db. The risk of noise induced hearing loss depends on both the intensity and duration of exposure. As intensity increases, the length of time for which the exposure is "safe" decreases.

Hearing protective devices, when involved in such loud activities or noisy recreational activities, must be properly selected and used to be a powerful tool for preventing NIHL. An analysis and history of prior art, emphasizes that proper selection and use, as the singular most important consideration for avoidance of NIHL. Earplugs, whether dynamic or manual, usually fail to produce the protection of the labeled rating because they are either not worn or placed correctly, or by neglect are not worn during the entire period of the noise exposure. It must be emphasized that the best hearing protector is not the one with the highest NRR, but the one that will consistently be worn whenever there is exposure to loud noise. There is no single protector that will fit everyone, be universally comfortable, and be appropriate in every environment.

Description of Related Art

An analysis of U.S. Pat. No. 7,512,243, reveals substantial differences from the present embodiment presented. Dynamic range limitation requires intervention by user to select a high or low range. This ear plug contains only a single filter whereas the embodiments I have presented, incorporate a dual filter element in combination with mechanical acoustic chamber to achieve a better dynamic range of performance without the need for user to make any range selection. With my proposed embodiment, the user would be able to move freely from a quiet area to a noisy one and still remain protected from excessive or harmful noise. With my embodiments, the need for manufacturing in multiple components is eliminated as is contained in this prior art method of manufacture claim. The elimination of the need to switch allows all the cavity's and mechanical shapes to be able to be contained within the body of the earplug itself, requiring the insertion of only the filter medium. This prior art design as stated has no ability or provision for interconnection to other communication systems A review of U.S. Pat. No. 6,148,821, reveals the design to have not only all of the differences shown above, but also it should be noted, that when the user selects maximum attenuation mode, this design effectively becomes a solid earplug with all the disadvantages inherent with a solid earplug, vie. problems with communications and the inability to hear warning signals.

The design of U.S. Pat. No. 5,113,967, is used primarily by musicians, and is intended to provide a fixed level of attenuation dependent on the model selected; the purpose is to provide a "natural" sound just at a lower level to the user. This device does not include any dynamic attenuation based on the input sound level. In addition, the frequency response is enhanced at the higher frequencies in order to provide the desired natural sound. My device is dynamic both in attenuation level based on sound level input and in the frequency shaping at higher sound level inputs, in order to increase the attenuation in the frequency range of 2k-6 KHz to help protect the ear in this most damage prone area to excessive sound. In addition, there is no provision for interconnection for radio or other communication devices.

SUMMARY

A review of the prior designs reveal those as having either manual mode switching via a selection of a high attenuation mode or low attenuation mode for communications, or a fixed rate of attenuation. A review of the prior art indicates the inability to hear critical sound including speech while filtering loud or harmful impact sounds.

The first embodiment presented addresses that issue and allows for communication without having the user to select either a switch position or physically changing the earplug. Operator intervention for use in differing noise environments are fully negated while full protection is obtained by the present embodiment and its many variations. Additional embodiments include the ability to hook up radio communication devices while in similar noisy environments, as well as for providing for custom molded embodiments of the protective earplug.

By incorporating not just one or two elements (resistant or damping) but rather five elements to achieve the nonlinear characteristics both in attenuation and frequency response shaping, the embodiments presented provide superior protection over a larger dynamic range, compared to all presently available prior art without any user intervention.

The Five elements shown are:
1. Item 16, secondary filter at sound source entrance,
2. Item 14, angular acoustically reflective and frequency shaping chamber,
3. Item 14, terminated into a unique sound passage as shown in FIGS. 3, 4, and 5,
4. Item 12, primary filter providing attenuation and frequency shaping,
5. Item 12, by having the end of the primary filter appurtenant to the ear canal to load the acoustic impedance of the ear canal thus providing acoustic damping and adsorption of the acoustic energy.

Advantages

The present embodiment and its variations have one or more aspects of the following advantages:
1. Non-electronic hearing protection designed to allow speech and communication while exposed to loud sounds, whether impact or continuous.
2. Advanced dynamic filtering technology for improving speech and communication without any distortion or muffling effect.
3. Automatic filtering that does not require human intervention or selection dependent upon external noise environment.
4. An earplug that can be used with one or two filters; the secondary filter is removable. A noise reduction rating of up to 12 db is possible with the use of only the primary filter, while a 22 db reduction is achievable with the use of both the primary and secondary filters.
5. Multi-functional dual filtered hearing protector designed to minimize impact or loud noises while allowing speech and communication.
6. Multi-functional dual filtered hearing protector that can be connected to portable radio devices including media/music players and communication devices as well as listening to speakers or other acoustic transducers.
7. The embodiment's design as contained in the earplug housing, is breathable and allows for pressure equalization.
8. The present embodiment and its elements can be inserted into custom fit designs.
9. The embodiments as contained in the earplug housing can easily be able to be fastened via the end stem to a retaining cord, in order to avoid loss or mis-placement.
10. The embodiment and its variations described are physically placed in earplugs of various sizes for a comfortable fit.
11. The embodiment and its variations described are of an ergonomic fit under helmets, etc.
12. The embodiment and its variations described can be used with cell phones or similar communication equipment.
13. The embodiment and its variations described are made of material that is comfortable, easy to use and clean and moisture resistant.

Other advantages of one or more aspects will be apparent from a consideration of the drawings and ensuing description.

FIGURES

In the drawings, closely related figures have the same number but different alphabetic suffixes.

FIG. 7 represents another embodiment wherein an attached "L" joint connector has replaced the removed secondary filter, as would be utilized for radio communications.

FIG. 8 is a view from the secondary filter end, demonstrating the removal of said secondary filter.

FIG. 9 is a view of another embodiment that shows a custom fit ear impression utilizing the molded chambers and dual filters inserted thereto.

FIG. 11 is a dual bar graph, one comparing the frequency response characteristics versus chamber pressure at ⅓ octave, and the other comparing the frequency response characteristics with a 4 port earplug body muffler only, no filters.

FIG. 12 is a dual bar graph of frequency response versus 4 port earplug; one graph typifies said response with both filters in front, while the other illustrates response with the 4 port earplug body muffler only, each filter in front.

FIG. 13 is a dual bar graph demonstrating the performance levels of all embodiments versus frequency, in one case with the 4 port earplug filter in front (ear side) only, and the other measuring the levels of performance versus frequency with the 4 port earplug in front and back.

FIG. 14 is a multiple bar graph response versus frequency of performance levels of all embodiments, at white noise levels of 70, 90 and 110 db inputs respectively.

FIG. 16 represents another embodiment wherein the filter as previously described is used in an alternative configuration for a communication headset.

FIG. 17 represents a visual concept of the theory of operation of the dual filtered earplug.

Figure 1:
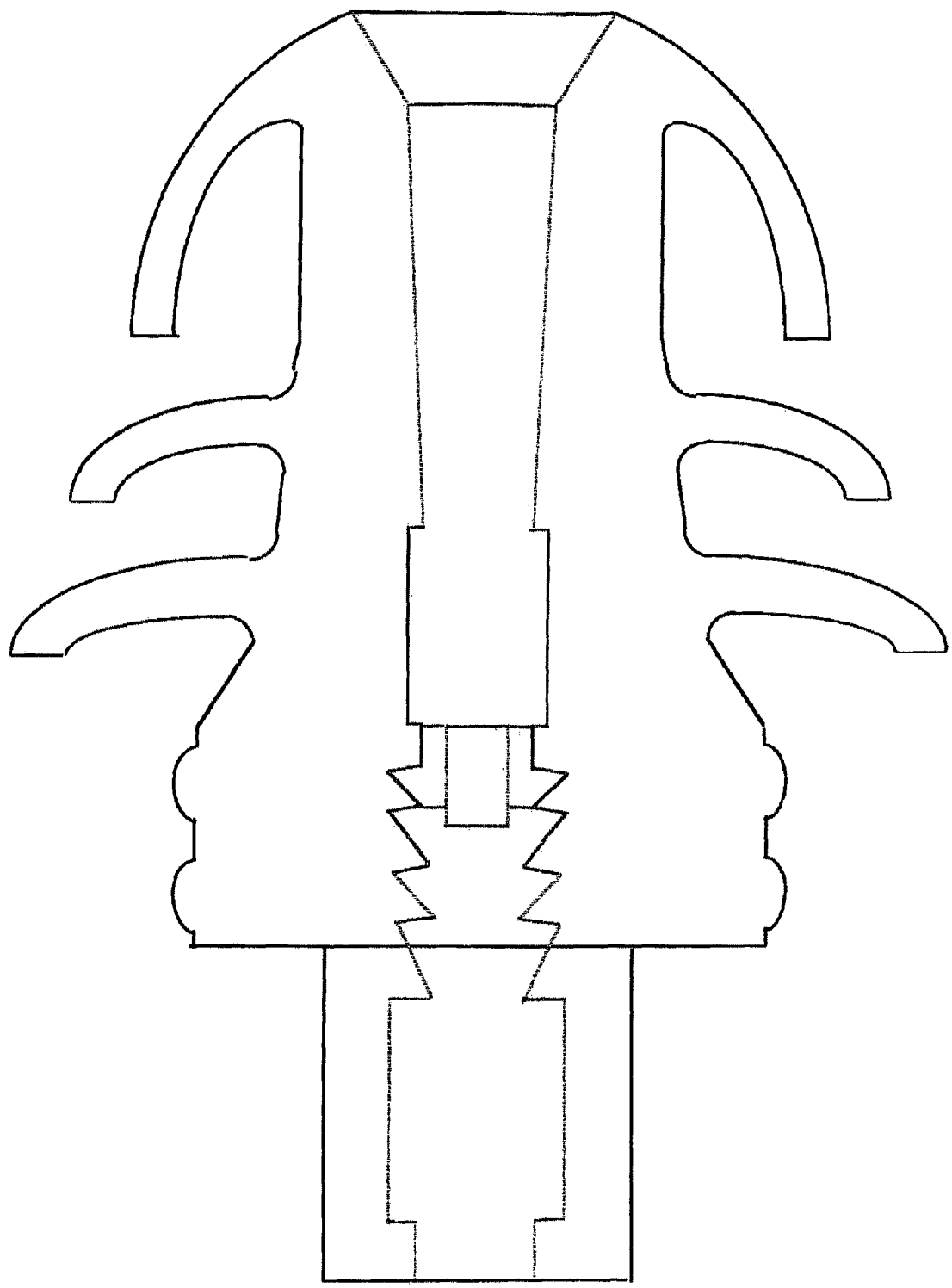
FIG. 1 represents a partially sectioned side view of the dual filtered earplug, showing the interior placement of the primary filter, the molded chamber angles, and the removable secondary filter.

REFERENCE NUMERALS 10 earplug housing
12 primary filter, 12 micron filter attenuator also used to reduce canal resonance
14 angular acoustically reflective and frequency shaping chamber
16 removable 25 micron secondary filter
18 removable Cord
20 "L" joint adapter

DESCRIPTION

Figure 2:
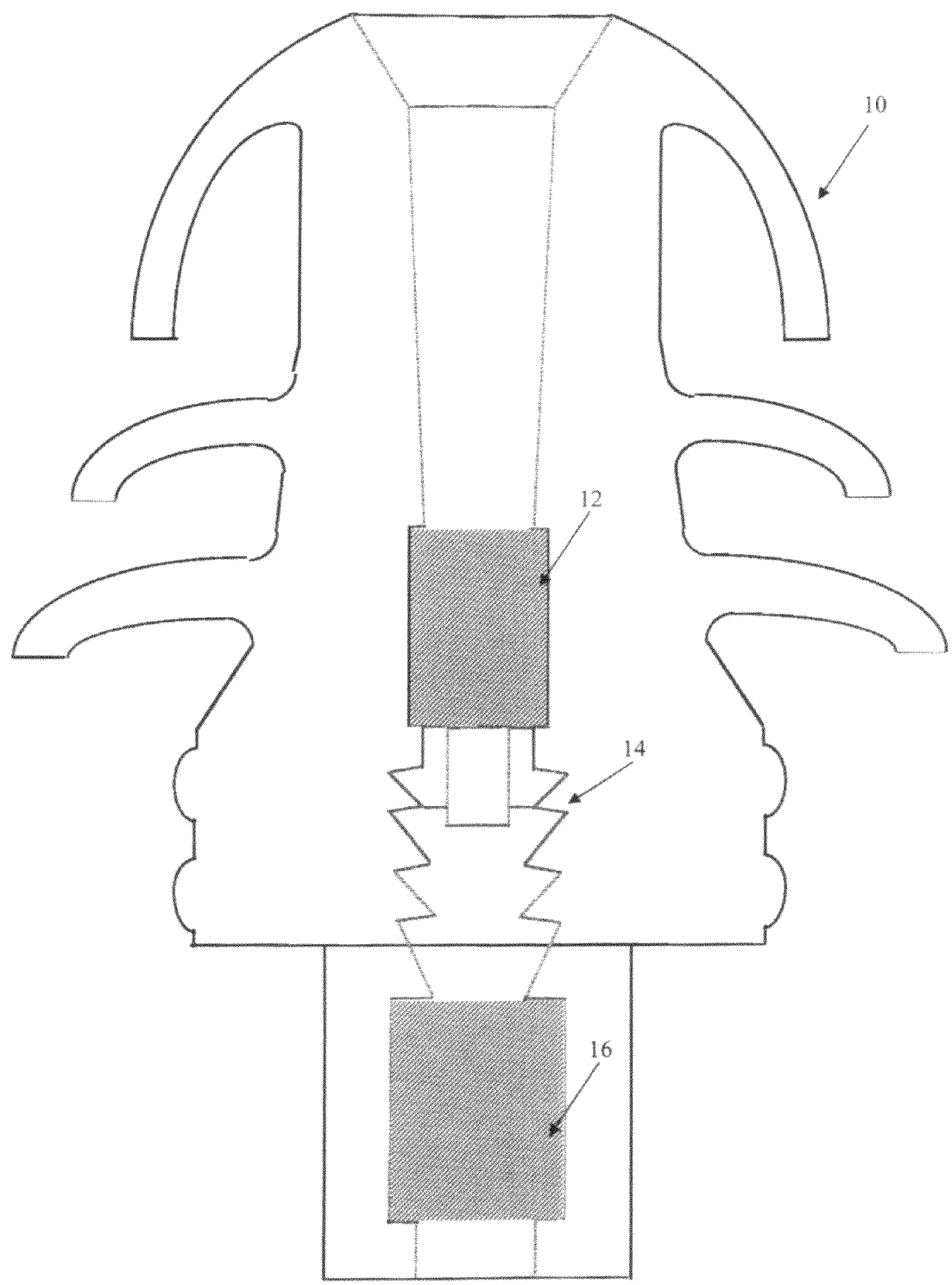
FIG. 2 is a detailed dimensional side view that shows all dimensions including the placement of the primary filter and the secondary filter.
Figure 3:
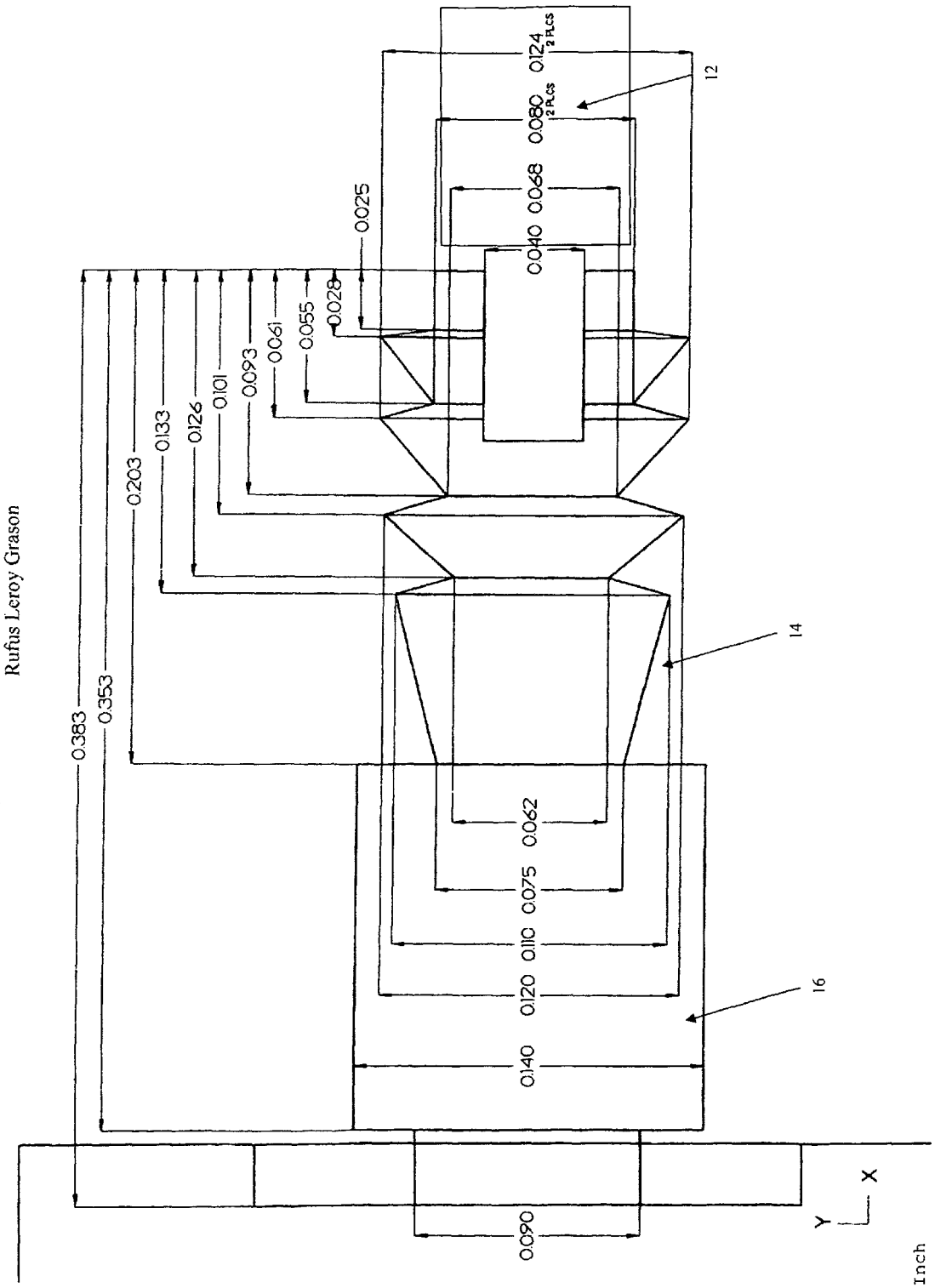
FIG. 3 is a detailed drawing that shows all of the respective chamber dimensions.

One embodiment of the dual-filtered hearing protector is illustrated in FIG. 1, FIG. 2 and FIG. 3. The earplug housing 10 containing this embodiment is inserted into the designated ear canal by grasping the exterior stem and placing the forward tip into the ear in a comfortable position. Prior to insertion, and for ease of removal, an attachment cord 18 may be positioned over the stem of the earplug housing 10, and tightened by a metal retainer. The purpose of this embodiment as contained in the earplug housing 10, is to reduce or eliminate loud sounds, including impact sound, while allowing audible speech signals or warning signals to be readily detected. This objective is achieved by the unique internal design as described below as well as illustrated in the drawings and figures accompanying this application.

Permanently contained in the dual filtered earplug housing 10, is a secondary or removable filter 16, in back of which is an angular acoustically reflective and frequency shaping chamber 14, which in turn channels sound waves to and through the primary fixed filter 12.

In order to remove the secondary filter 16, either to alter attenuation or provide for insertion of the "L" joint adapter 20 for radio hookup, one would stretch the outer lip of the stem until said secondary filter 16 can be released from the exterior port. This action would be repeated in reverse order to replace said secondary filter 16.

For custom fit applications, the primary filter 12 as well as the angular acoustically reflective and frequency shaping chamber 14 would be permanently inserted into a custom fit ear impression. This second embodiment when used in conjunction with a custom fit ear impression, presents a unique and heretofore unachievable method as it relates to human interaction and comfort. As with the first embodiment of the earplug 10, the removable secondary filter 16 would be inserted into the customized ear plug housing. After customization, no operator intervention would be required other than the optional insertion and removal of the secondary filter 16.

Figure 15:
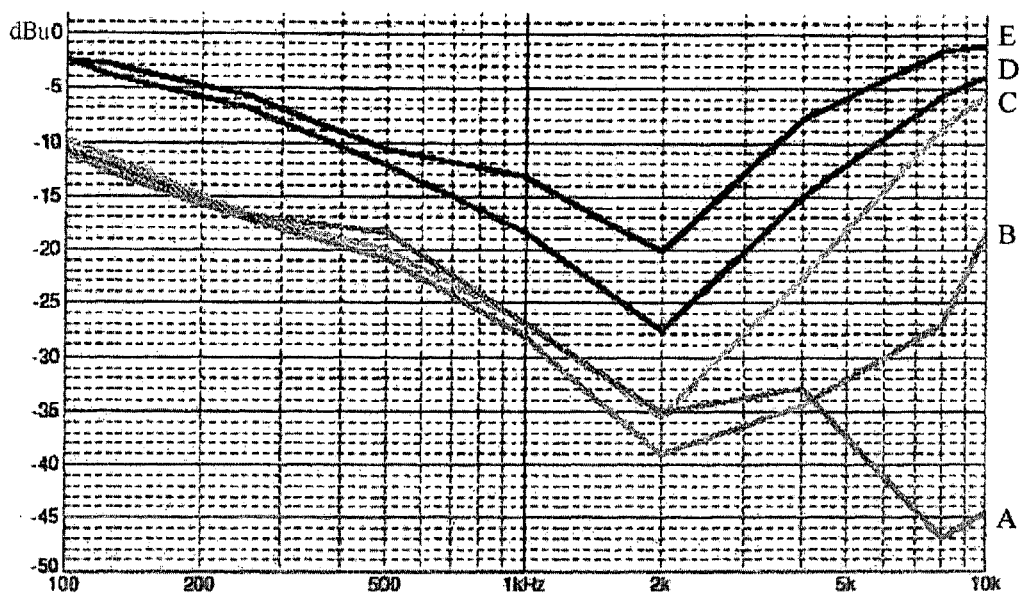
FIG. 15 is a frequency response chart demonstrating the frequency filtration performance of all embodiments with both filters utilized from 50 db to 110 db.

Whether contained in the provided ear plug housing or a customized unit, all embodiments contain two filters in addition to an angular pathway or acoustic labyrinth that operates as a channel to connect or interact as an acoustically resistive pathway between both the primary filter 12 and the removable secondary filter 16. The primary filter 12 is more resistant to the louder noise or sound. In operation, the primary filter 12 in combination with the angular acoustically reflective and frequency shaping chamber 14, provides the majority of the non linear attenuation and frequency shaping with changes in input levels as demonstrated by FIGS. 13, 14, 15 and effectively reduces ear canal resonance. In use, the sound would first pass through the removable secondary filter 16. The sound would then pass through the angular acoustically reflective and frequency shaping chamber 14. Finally the sound would pass through the primary filter 12. The process of passing through this complex channel will significantly diminish or mitigate peak sound pressure levels. The embodiment of the invention will cause cancellation or acoustic reduction dependent upon the characteristics and level of the incoming sound. Essentially, the mechanical filter as used in all embodiments is built as a dynamic attenuator/frequency shaping network, so that those frequencies contained in loud or impact sound waves, to which the ear is most sensitive, or that could expose the ear to damage would be substantially diminished.

Figure 4:
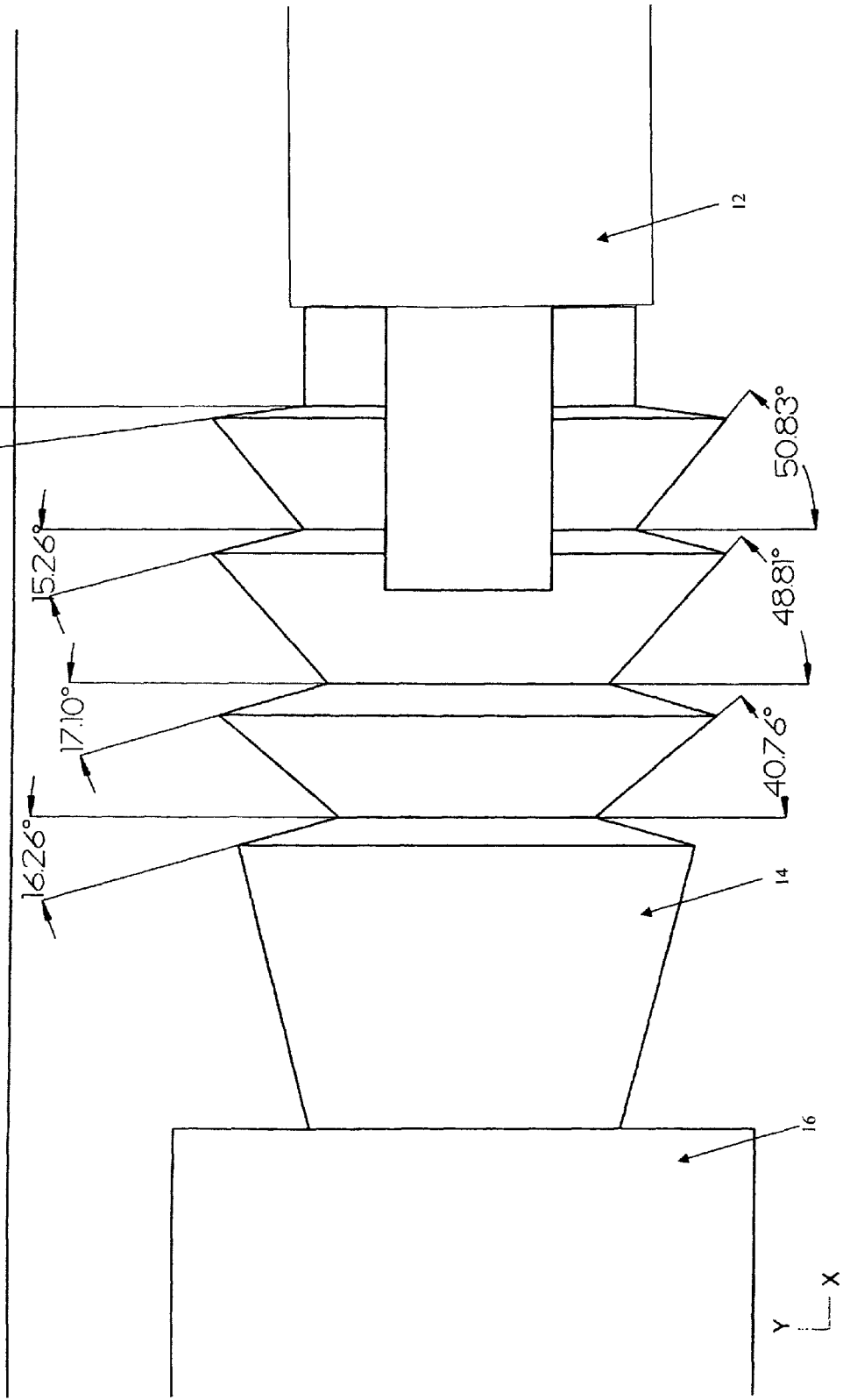
FIG. 4 is an enlarged side view that shows the respective angular dimensions of the chamber angles.
Figure 5:
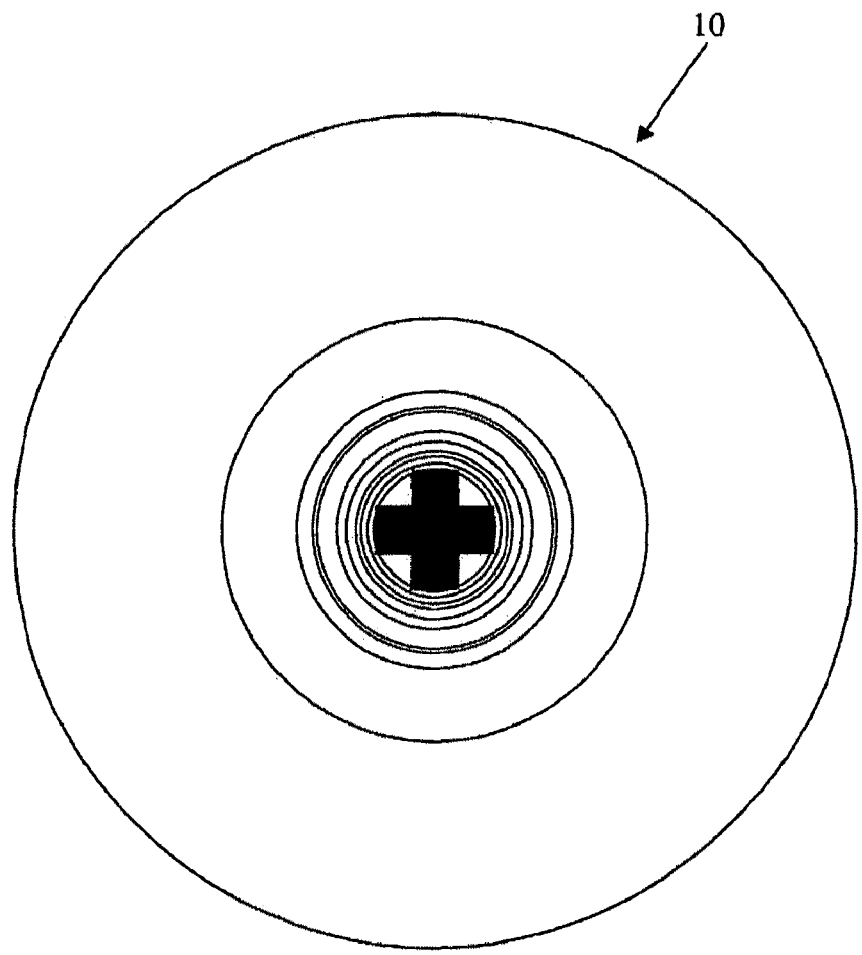
FIG. 5 represents a cross section end view that demonstrates the interior concentric canals.
Figure 6:
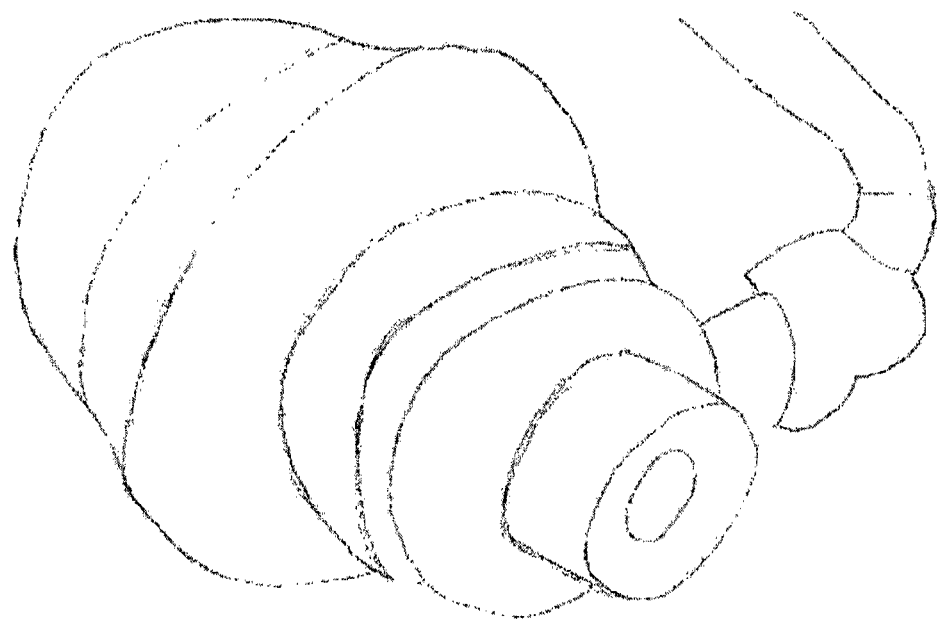
FIG. 6 is a representation of one of the earplugs containing the present embodiment with a removable cord attached.
Figure 10:
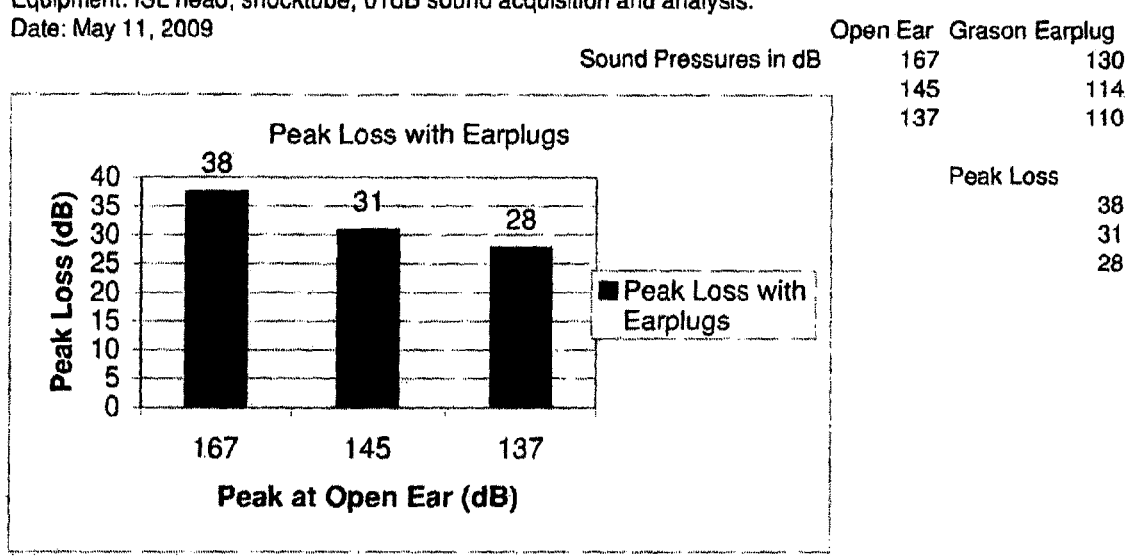
FIG. 10 is a chart demonstrating insertion loss by filter.

This filtration, as performed by the primary confluence of the primary filter 12 and the removable secondary filter 16, is dynamic. Noise filtration is embodied in the design of the angular acoustically reflective and frequency shaping chamber 14, as well as the primary 12 and secondary 16 filters. The dual filtered earplug 10, containing the internal angular acoustically reflective and frequency shaping chambers, FIG. 4, represents a self-contained, single unit and other than the optional removal of the secondary filter 16, there are no additional parts. This dynamic operation and self-contained single body construction distinguishes this device from prior art.

Operation

As previously described, the static and dynamic noise filtration and suppression characteristics of all embodiments are contained in either the standard earplug type housing 10, or a customized ear mold. The only element that can be altered by operator intervention is the secondary filter 16. The secondary filter 16 is located at or near the exterior port. The secondary filter 16 may either be removed to alter attenuation, replaced with a solid plug, or replaced with an "L" joint adapter for communication purposes, or left in for normal operation of the hearing protector.

To hook up to radio communication, a feature mainly for law enforcement, military, security, and industrial applications, the "L" joint adapter 20 would be inserted in place of the exterior external filter 16. Radio tubing will then be attached to the external end of the "L" joint adapter 20.

The multi-filtered earplug housing 10 is manufactured in various sizes to enable users to select the appropriate size for ergonomic fit and comfort. The multi-filtered earplug as designed, collectively forms an acoustically resistive labyrinth pathway to diminish high level impulse or high level sound, while still allowing sound to pass at reduced levels. Accordingly, the user is able to distinguish speech or other communication in a chaotic sound environment. The physical design and subsequent operational acoustic characteristics of the multi-filtered earplug, creates a frequency drop-off as the input sound pressure levels increase in those frequency spectrum of sound, that have been shown most probable to cause noise induced damage to the ear. As can be seen by the attached drawings as well as the acoustic frequency response data, the filter characteristics of the embodiment operates as a dynamic isolation network minimizing damaging loud and impact noise while allowing sound to be heard at a reduced level, helping to protect the ear from noise induced hearing loss. What is unique about the present embodiment, as compared to prior art, is that its operation is dynamic, non-electric and does not require human interference or selection. The present embodiment represents a self contained and single unit of ear protection. Other than the optional removal of the secondary filter 16, there are no additional parts. Prior art describes filters that require operator intervention or selection for the desired filtration characteristics. The present embodiment is contained in a earplug housing 10, as a single unit and encompasses dynamic response built into this one unit rather than by or through several pieces or parts.

Alternative Embodiments

Another embodiment consisting of the primary filter 12, the interconnecting angular acoustically reflective and frequency shaping chamber 14, and the removable secondary filter 16, may be molded into or inserted as a singular pre-made custom fit unit.

The earplugs, ear molds or electronic devices containing the described first embodiment may be made in various colors, sizes or materials dependent upon the needs and applications of the user.

Additionally, a more comfortable, improved and more efficient earplug, can be manufactured by using the available method of obtaining an impression of the ear canal by the use of instant set materials or the creation of a laboratory produced custom ear mold and creating a custom device containing the first embodiment. This process would incorporate not only the filters 12 and 16, but also the interconnecting angular acoustically reflective and frequency shaping chamber 14, manufactured as separate pieces and assembled within a custom ear mold or electronic device, while maintaining the design described in the first embodiment. Variation of the method of customization process and technique will incorporate the acoustic structure as described and would be useful when the hearing protection requires higher levels of attenuation or comfort for use over extended periods of time.

A behind the ear device (BTE) or in canal device containing elements of the first embodiment could also be incorporated and used for communication headsets or active electronic noise reduction. Since these alternative embodiments could be manufactured of higher density material, a higher attenuation value would be achieved, given proper fit and use. The close proximity of the sound source to the ear, will allow the wearer to hear communication and warning sound recognition while suppressing the local loud or impact sounds.

Other customized, multi-functional designs incorporating the elements of the first embodiment, could be envisioned in applications for various communication configurations and/or listening devices.

The multi-filtered earplug may be used in a standard off the shelf product or may be custom fit for specific applications, ie. motorcyclists, construction crews, military, law enforcement or industry. In every circumstance where the ability to function in a noisy environment is critical, while still being cognizant of the activity in the surrounding area, the user's hearing will be protected.

Although the description above contains many specificities, these should not be construed as limiting the scope of the embodiments but as merely providing illustrations of some of several embodiments. Thus, the scope of the embodiments should be determined by the appended claims and their legal equivalents, rather than by the examples given.

I claim:

1. A hearing protection ear plug comprising a shell to be placed in an ear canal of a user, an output port of said shell communicating with said ear canal entrance, a sound source entrance port channeling input sound to a small chamber communicating with an acoustic filter, output of said acoustic filter directing said sound into a frequency shaping chamber containing multi-angular and multi-reflective sides, whereby there occurs a non-linear cancellation and acoustic reduction depending upon characteristics and levels of said incoming sound, said shaping chamber having an output port communicating with a primary attenuating filter whose output then communicates with a output port of said shell whereby sound transmitted at said ear canal entrance has been dynamically modified to allow voice and critical communication while attenuating noise and loud impact sound, without the need of any operator intervention.

2. The hearing protection ear plug as defined in claim 1, wherein the input filter has been removed from the shell allowing a larger sound source entrance chamber.

3. The hearing protection ear plug as defined in claim 1, wherein the input filter has a pore size of 25 microns.

4. The hearing protection ear plug as defined in claim 1, wherein the primary attenuating filter has a pore size of 12 microns.

5. The hearing protection ear plug as defined in claim 1, wherein the input filter has been removed from the shell and replaced by a pre-molded tubular extension, enabling the attachment of communication devices or other acoustic transducers.

6. A hearing protection ear plug according to claim 1, wherein said input filter, primary attenuating filter, and interconnecting angular acoustically reflective and frequency shaping chamber are custom fit for a standard hearing device.

7. A hearing protection ear plug according to claim 6 wherein the input filter has a pore size of 25 microns.

8. A hearing protection ear plug according to claim 6, wherein the primary attenuating filter has a pore size of 12 microns.

9. A method of manufacture of a custom hearing protector according to claim 6, said method to incorporate not only the important primary attenuating filters, but also the interconnecting angular acoustically reflective and frequency shaping chamber.

* * * * *